United States Patent
Densham

(10) Patent No.: US 6,623,929 B1
(45) Date of Patent: Sep. 23, 2003

(54) POLYNUCLEOTIDE SYNTHESIS USING A PROCESSING ENZYME

(75) Inventor: Daniel Henry Densham, Devon (GB)

(73) Assignee: Medical Biosystems, Ltd. (GB)

( * ) Notice: Subject to any disclaimer, the term of this patent is extended or adjusted under 35 U.S.C. 154(b) by 0 days.

(21) Appl. No.: 09/937,800

(22) PCT Filed: Apr. 6, 2000

(86) PCT No.: PCT/GB00/01289

§ 371 (c)(1),
(2), (4) Date: Jan. 2, 2002

(87) PCT Pub. No.: WO00/60072

PCT Pub. Date: Oct. 12, 2000

(30) Foreign Application Priority Data

Apr. 6, 1999 (GB) ............................................... 9907813

(51) Int. Cl.⁷ ........................... C12Q 1/68; G01N 33/53; C07H 21/04; C12P 19/34
(52) U.S. Cl. ........................... 435/6; 435/7.6; 435/91.1; 536/24.32; 536/24.3
(58) Field of Search ........................ 435/6, 91.1, 91.2, 435/7.9, 7.6; 536/24.3, 24.33

(56) References Cited

FOREIGN PATENT DOCUMENTS

| | | |
|---|---|---|
| EP | 0 655 506 A1 | 5/1995 |
| EP | 0 669 395 A2 | 8/1995 |
| EP | 0 727 496 A2 | 8/1996 |
| WO | WO 90/05303 A1 | 5/1990 |
| WO | WO 97/09451 A1 | 3/1997 |
| WO | WO 97/26368 A1 | 7/1997 |
| WO | WO 98/40496 A1 | 9/1998 |
| WO | WO 98/40496 * | 9/1998 |
| WO | WO 99/05315 A2 | 2/1999 |
| WO | WO 99/10366 A1 | 3/1999 |

* cited by examiner

Primary Examiner—Kenneth R. Horlick
Assistant Examiner—Cynthia Wilder
(74) Attorney, Agent, or Firm—Saliwanchik, Lloyd & Saliwanchik

(57) ABSTRACT

The present invention pertains to a method for polynucleotide synthesis, comprising the steps of: (i) reacting a polynucleotide processive enzyme, e.g., a polymerase or TdT, with a nucleotide substrate under conditions suitable for enzyme activity; and (ii) modulating the conformation of the enzyme, e.g. using radiation, to allow incorporation of a predetermined nucleotide.

5 Claims, No Drawings

POLYNUCLEOTIDE SYNTHESIS USING A PROCESSING ENZYME

FIELD OF THE INVENTION

This invention relates to a method for polynucleotide synthesis.

BACKGROUND OF THE INVENTION

At present the demand for synthetic polynucleotides is large, due in most part to the need for oligonucleotides of known sequence to be used as primers within the Polymerase Chain Reaction (PCR) or within polynucleotide sequencing strategies. More recently, demand has increased even further with the advent of polynucleotide hybridisation arrays. These arrays have, attached to a solid support (or chip), either oligonucleotide probes that hybridise with the sample to be tested, or sample to which labelled oligonucleotide probes can hybridise (Lysov, Dovi. Akad. Nauk SSSR (1988) 303:1508–1511; Bains et al, J. Thero. Biol., 135:303–307; Dramanac et al, Genomics, 4:114–128). This hybridisation pattern is then used to reconstruct the target polynucleotide sequence. This technique has been further facilitated by the utilisation of light-generated oligonucleotide arrays (Fador et al, Proc. Natl. Acad. Sci. USA (1994) 91:5022–5026).

All current techniques are restricted in the length of synthetic polynucleotide that can be produced and the accompanying problem of low yields. They also employ a significant number of manipulations and hence take a significant period of time to execute.

There is therefore a need for an improved method for the synthesis of polynucleotides which significantly increases the maximum length of the polynucleotide synthesised and increases the rate at which such a polynucleotide is synthesised. Such a process would preferably be carried out by an automated process, reducing the complexity and cost associated with existing methods.

SUMMARY OF THE INVENTION

The present invention is based on the realisation that electromagnetic radiation can be used to generate conformational changes within a polynucleotide processive enzyme, such that by controlling the radiation applied to such an enzyme, the sequence of the polynucleotide strand produced can be pre-determined. This enables the production of "synthetic" polynucleotides in real-time by manipulating the normal in vivo polynucleotide assembly process.

According to the present invention, a method for synthesising a polynucleotide comprises the steps of:

(i) reacting a polynucleotide processive enzyme with a nucleotide substrate under appropriate conditions; and (ii) exposing the enzyme to a controlled environment (including radiation) so as to affect the three-dimensional conformation of the enzyme and hence determine/affect the sequence of the polynucleotide produced.

DESCRIPTION OF THE INVENTION

If radiation is used to control the conformation of the processive enzyme, then it may be applied to a sample using a number of techniques. These include evanescent wave spectroscopy techniques, in particular surface plasmon resonance (SPR) spectroscopy.

The application of radiation to the processive enzyme via the application of laser technology (Light Amplification by Stimulated Emission of Radiation) is particularly applicable to the present invention due to the monochromatic and controllable nature of the radiation produced by such devices.

The control of the conformational structure of processive enzymes can be accomplished by controlling the environment in which they act It has been shown that variations in such conditions as pH and sait content/concentration of the reaction medium can have an effect on the three-dimensional structure and hence on the activity of such enzyme systems (Wong et al, Biochemistry (1991) 30:526–537).

The addition of the specified nucleotide, and hence the synthesis reaction, may be accomplished by directly creating the ability of the processive enzyme to undergo a conformational change that IS specific for the addition of a particular nucleotide, depending on the form of radiation delivered. This could be achieved by engineering (via state-of-the art genetic manipulation techniques) a processive molecule (or molecule associated with it) such that it contained a chemical/moiety/peptide group or groups that enable the molecule to convert or transduce radiation into a conformational change. These chemical/moiety group or groups may be so positioned so as to select for the nucleotide to be added to the growing polynucleotide chain. The method may therefore proceed on a "real-time" basis, to achieve a high rate of polynucleotide synthesis.

The present method for the synthesis of a polynucleotide, as indicated above, involves the control of the environment in which a polynucleotide processive enzyme is placed, and hence of the three-dimensional conformation of said enzyme. This three-dimensional conformation in turn selects if and/or which substrate nucleotide is added to the growing polynucleotide strand.

The term "polynucleotide" is used herein as to be interpreted broadly, and includes DNA and RNA, including modified DNA and RNA, as well as other hybridising nucleic acid-like molecules, e.g. peptide nucleic add (PNA).

The term "polynucleotide processive/polymerisation enzyme" is used herein as to be interpreted broadly, and pertains to ubiquitous proteins that can attach one nucleotide to another in order to create a polynucleotide. Such a group will, of course, include all polymerases, both DNA- and RNA-dependant and also such enzyme groups as terminal deoxynucleotidyl transferases (Kato et al, J. Biol. Chem., (1967) 242:2780; & Frohman et al, Proc. Natl. Acad. Sci. USA, (1988) 85:8998).

Using a polynucleotide processive enzyme in order to control the synthesis of a polynucleotide offers several advantages for the success of this method. Firstly, the problem of reaction yield in solid phase synthesis is avoided due to the highly efficient catalytic nature of organic molecules. Secondly, speed of synthesis and polynucleotide strand length are several orders of magnitude greater than those currently available, again due to the requirements of the enzyme systems in their native environments.

Another important aspect of the invention is the realisation that, although a large number of polynucleotide processive enzymes require an existing polynucleotide template to initiate polynucleotide synthesis in their native environment/form, this is not always the case. As the effectiveness of the nucleotide (Crick-Watson) base pairing and hence of complementary strand construction is ultimately dependent on the three-dimensional conformation (and resulting kinetic parameters) of the processive enzyme, this system can be disrupted and utilised in order to externally control the sequence of nucleotides polymerised. In the specific case of the utilisation of polymerases for the present invention, therefore, the "synthetic" polynucleotide strand produced may not (and in most instances will not) be a complementary copy of the template polynucleotide strand. Disruptions to polymerase function via active site mutation are known in the art (Freemont et al, Proteins (1986) 1:66–73) but, critically, they are not conformationally/ spatially modulated. Such disruption/mutation could take the form, as in the present invention, of a reduction in the natural fidelity of the polymerase such that it does not discriminate against dideoxynucleotides. This would allow the mutated polymerase to insert any nucleotide in solution into the growing polynucleotide chain independently of the nucleotide sequence of the polynucleotide template. The nature of such binding site modifications that are fixed upon molecular cloning (i.e. not capable of external real-time conformational modulation) are known in the art (Ollis et al, Nature (1985) 313:762–766 & Freemont et al, Proteins (1986) 1:66–73) and are directed at the polymerase active site. For example, it has been shown that $Phe^{762}$ of E. Coli polymerase I is one of the amino acids that directly interact with the substrate nucleotide (Joyce et al, Ann. Rev. Biochem. (1994) 63:777–822 & Astake et al, J. Niol. Chem. (1995)270:1945–54). Converting this amino acid to a Try results in a mutant DNA polymerase that does not discriminate against dideoxynucleotides. See U.S. Pat. No. 5,614, 365 and copending U.S. application Ser. No. 08/525,087, of Deb K. Chatterjee, filed Sep. 8, 1995, entitled "Mutant DNA Polymerases and the Use Thereof", which are expressly incorporated herein by reference.

These modifications have since been characterised further in order to define polymerases with reduced error rate, that is reduced misincorporation of nucleotides during nucleic acid synthesis and/or increased fidelity of polymerisation. See WO-A-99/10366, which is expressly incorporated herein by reference. This application relates to a method of making such high fidelity polymerases by modifying or mutating the nucleotide binding domain of the polymerase (e.g. the O-helix).

An important aspect of the method of the present invention is the use of a protein/peptide/chemical group/moiety that has a structure/conformation capable of being modulated via interaction with photons and/or energy derived from photons. Such groups include, but are not limited to, biological molecules which transduce photonic energy, synthetic dye compounds, and energy-absorbing chemical groups. A preferred embodiment of the present invention involves the utilisation of biological photonic transducers to modulate the polymerase active site (e.g. O-helix) conformation and hence polymerase activity. This group of biological transducers includes, but is not limited to, light-harvesting (LH) complexes/molecules and systems involved photosynthesis (e.g. bacterial complexes such as LH1 and LH2; see Papiz et al, Trends Plant Sci. (1996) 1:198–206), direct photon-driven proton pump complexes/subunits (e.g. bacteriorhodopsin (BR) from the purple membrane of Halobacterium salinarium; see Oka et al, Biophy. J. (1999) 76:1018–1023), sensory pigments, (e.g. retinal and associated protein complexes) and natural fluorescent proteins and the engineered derivatives (e.g. Green Fluorescent Protein (GFP); Heim et al, Proc. Natl. Acad. Sci. USA (1994) 91:12501–12504).

The active sites of polymerase molecules which affect overall function and are targeted for controlled conformational modulation within the present invention, include, but are not restricted to, the O-Helix, the K-helix, and the inter O-P loop of Taq DNA polymerase or analogous positions in other polymerases; see WO-A-98/40496.

Methods for genetically "fusing" the sequences and hence structures of two or more peptides/proteins are well known in the art and have been applied extensively in the case of Green Fluorescent Protein (GFP) to construct fused mutant or "chameleon" proteins to create fluorescent labels for specific substrates such as $Ca^{2+}$ and to modulate spectral response (Heim et al, Proc. Natl. Acad. Sci. USA (1994) 91:12501–12504 & Heim et al, Nature (1997) 388:882–887).

In a preferred embodiment, the O-helix of T7 polymerase is fused to a fluorescent mutant of GFP. This results in a fusion protein whose nucleotide substrate affinities can be modulated in response to exposure to differing wavelengths of light and the sub-type of GFP mutation chosen.

In a further preferred embodiment, the photon-transducing protein and the polymerase are cloned separately and reactive side groups capable of taking part in cross-linking reaction(s) are site-selectively introduced into each protein structure at the desired location (e.g. the O-helix within the polymerase).

A number of strategies may be used to attach reactive groups to the proteins. Strategies include, but are not limited to, the use of site-directed mutagenesis and unnatural amino acid mutagenesis (Anthony-Cahil et al, (1989) Trends Biochem. Sci. 14:400) to introduce cysteine and ketone handles to act as a site for cross-linking to occur. Cross-linking reagents which contain two reactive groups can then be employed to covalently link the chosen side groups (Haugland, Handbook of Fluorescent Probes and Research Chemicals, $6^{th}$ Edition, Molecular Probes, p94–106). Examples of such cross-linking reactions include thio (derived from cysteine)-thiol cross-linking, amine-amine cross-linking, amine-thiol cross-linking, amine-carboxylic acid cross-linking, amine-carbohydrate cross-linking and thiol-carbohydrate cross-linking.

As already outlined, it is foreseen that in some circumstances the presence of an existing polynucleotide strand may not be necessary for template-directed synthesis to take place at all. For example, this would be possible using extensively modified polymerases that have been cloned to "design" via state-of-the-art recombinant genetic techniques. As stated previously, the conformation of these polymerases would be under external control (preferably a radiation source) and this external manipulation of the enzyme's nucleotide substrate specificity determines the growing polynucleotide's polymerisation sequence. Moreover, certain groups of polynucleotide synthetic enzymes do not require starting polynucleotide templates for synthesis, even in their "native" environment. Such a group is the terminal deoxynucleotidyl transferase group of enzymes. Terminal deoxynucleotidyl transferase (TdT) catalyses the repetitive addition of mononucleotides from a deoxynucleoside triphosphate to the terminal 3'-hydroxy of a DNA initiator, with the release of inorganic phosphate. The enzyme requires an oligodeoxynucleotide containing at least three phosphate groups and a free 3'-OH to serve as initiator.

In a further embodiment of the invention, therefore, a free 3'OH group extending from a solid support will act as an initiator for the TdT and the engineered enzyme will synthesise a polynucleotide via the addition of substrate nucleotides via the control of radiation applied to the enzyme. In a simpler, but slower, embodiment of this system, the enzyme could be made (via genetic engineering or control of reaction conditions) to polymerise any nucleotide available as substrate and hence control of the nucleotide present in solution would determine the sequence of the polynucleotide synthesised.

In another embodiment of the invention, the TdT or polymerase (or any other polynucleotide polymerase) is bound to a solid support and the nucleotides and/or radiation are made available to the enzyme whilst bound. This embodiment allows the user to localise the application of radiation and/or substrate and grow the new polynucleotide strand into solution. This configuration of the invention has the added advantage that, once the desired polynucleotide has been synthesised, it can be released from the bound enzyme and the process begun again (i.e. it is a regenerative process).

A preferred embodiment of the invention involves the localisation of the polynucleotide processive/polymerase enzyme system in space. This localisation may take the form of, but is not restricted to, immobilisation on a solid support. Localisation of the polymerase in space offers several important advantages for the success of this method. Firstly, the problem of unwanted attenuation of the applied radiation/controlled environment is reduced as the exact location of the polymerase in space is known and can hence be more easily selectively controlled via localised environmental modulation (e.g. laser pulses). Secondly, unwanted/uncontrolled interaction (or random energy attenuation) of the enzyme system with the local environment/substrate (e.g. nucleotides) not directly involved with the polymerase is reduced considerably. This is particularly relevant if radiation (e.g. photonic) is utilised, as envisioned within the scope of the invention, to control/attenuate the conformational form of the polymerase.

Immobilisation may be carried out using standard procedures known in the art. In particular, immobilisation using standard amine coupling procedures may be used, with attachment of ligand-associated amines to, say, a dextran or N-hydroxysuccinimide ester-activated surface. In a preferred embodiment of the invention, the polymerase is immobilised onto a SPR sensor chip surface where changes in the refractive index may be measured. Examples of procedures used to immobilise biomolecules to optical sensors are disclosed in EP-A-0589867, and Löfas et al, Biosens. Bioelectron. (1995)10: 813–822.

Localisation within space can also be carried out, and is a further embodiment of the invention, via the utilisation of a Laser Tweezer or Optical Trap System (Sheetz, Ed., *Laser Tweezers in Cell Biology*, Vol.55 of *Methods in Cell Biology* (Academic Press, New York, 1997)). Optical Tweezers exploit the fact that light exerts force on matter. Dielectric particles, such as uniform beads or bacterial cells, are attracted to and trapped near the waist of a laser beam that has been focused through a microscope objective. Applied forces will displace a trapped bead from the trap centre, with a linear dependence of displacement on force. Biological molecules such as polymerases, as within an embodiment of the present invention, can be bound to polystyrene or silica beads, which are usually ~1 µm in diameter. The trap can then be used to steer the immobilised polymerase into the desired experimental geometry/controlled environment within the reaction flow cell.

Thee polynucleotide polymerisation enzyme used in the invention may be of any known type. For example, a polymerase may be any DNA-dependant DNA polymerase, e.g. T7 gene 5 polymerase or Taq polymerase. If the target polynucleotide is an RNA molecule, then the polymerase may be an RNA-dependent DNA polymerase, i.e reverse transcriptase or a RNA-dependent RNA polymerase, i.e. RNA replicase. TdT is preferred.

Nuclear Magnetic Resonance (NMR) Spectroscopy (Bradley et al, J. Mol. Biol., (1990) 215:607–622) and Electron Paramagnetic Resonance (EPR) Spectroscopy (Todd et al, Biochemistry, (1991) 30:5515–5523) are further preferred methods of subjecting the polynucleotide polymerisation enzyme to specific types of radiation to control specific nucleotide addition via conformational control and at the same time allow structural/conformational data feedback. Using this technique it is also possible to measure the response of the enzyme molecules. NMR spectroscopy measures the magnetic properties of compounds. Nuclei of compounds are energetically orientated by a combination of applied magnetic field and radio-frequency radiation. When the energy exerted on a nucleus equals the energy difference between spin states (the difference between orientation parallel or anti-parallel to the direction of the applied fields), a condition known as resonance is achieved. The absorption and subsequent emission of energy associated with the change from one spin state to the other, are detected by a radio-frequency receiver.

In yet another embodiment of the invention, the starting 3'OH group is attached to a bead (e.g. one end of the biotin could be biotinylated and attached to a streptavidin-coated polystyrene sphere; Chu et al, Optical Society of America, Washington, D.C., (1990), 8:202) and held within an optical trap (Ashkin et al, Opt Lett. (1986) 11:288) within a flow cell (as outlined previously). As the polynucleotide processive enzyme (under external control) synthesises new polynucleotide, this new polynucleotide can be moved in space via the optical trap (or also known as optical tweezers) and hence keep the processive enzyme within the field of detection. It is also envisaged that this system could work in the reverse set-up with the bound polynucleotide processive enzyme being held by the optical trap.

The following Example illustrates the invention.

EXAMPLE

The following analysis was carried out on a modified BIAcore® 2000 system (Biacore AB, Uppsala, Sweden) with a sensor chip CM5 (Research grade, BIAcore AB) as the optical sensor/control/reaction surface. The instrument was provided with an integrated µ-fluidic cartridge (IFC) which allows analysis in four cells by a single sample-injection.

Preparation of Cysteine-tagged Bacteriorhodopsin

Bacteriorhodopsin (BR) is a light-driven proton pump in the purple membrane of *Halobactetium salinarium*. The photocycle of BR is initiated by absorption of a photon by the retinal chromophore. The site-specific mutation $Ile^{222} \rightarrow Cys$ (cysteine mutation) was introduced (Erlanson et al, Tetrahedron (1997) 53:12041) into the bop gene. According to the current structural model of bacteriorhodopsin (Lanyi et al, Science (1999) 286:255–260), $Ile^{222}$ is located at the cytoplasmic end of helix G. X-Ray Diffraction studies (Lanyi et al, Science (1999) 286:255–260) and Heavy Atom Labelling (Lanyl et al, Biophys. J. (1999) 76:1018–1023) show major structural/conformational changes within helix G associated with photonic absorption. The changed bop gene was constructed by inserting it into a non-integrating vector, with novobiocin resistance as the selective marker. *Halobacterium salinarium* was transformed as described by Ni et al, Gene (1990) 90:169–172 & Needleman et al, J.

Biol. Chem. (1991) 266:11478–11484. The mutated protein was purified from *H. salinarium* as purple membrane (PM) sheets according to the standard method described by Oesterhelt and Stoeckenius., Methods Enzymol. (1974) 31:667–678.

Preparation of Cysteine-tagged T7 Polymerase

An expression vector containing T7 polymerase coding sequence was constructed. A site-specific mutation was introduced (Erlanson et al, Tetrahedron (1997) 53:12041) into the O-helix coding region at $Arg^{518} \rightarrow Cys^{518}$. Cell pellets were lysed with a French press, and the enzyme was purified by Ni-nitrilotriacetic acid affinity chromatography, followed by cation exchange chromatography (sulfopropyl-Sepharose fast flow) and a final step of size-exclusion chromatography (Superdex 200).

Thiol-thiol Cross-linking Reaction

10 $\mu$M of mutated T7 and 10 $\mu$M of mutated bacteriorhodopsin were added to Hepes (10 mM Hepes, 150 mM NaCl, 0.05% surfactant P20 (BIAcore AB, Uppsala, Sweden), pH 7.4) buffer solution containing 2 mM $\beta$-mercaptoethanol (which was added to increase the specificity of cross-linking). After a 2-hour incubation at 25° C., the cross-linking reaction was quenched by the addition of a thiol-capping reagent, methyl methanethiolsulfonate (20 mM), and the products were confirmed by SDS-polyacrylamide gel electrophoresis (SDS-PAGE) under non-reducing conditions. The bacteriorhodopsin-polymerase complex was then purified by anion-exchange chromatography on Mono-Q and then resuspended in Hepes Buffer (complex at 8 mg/ml).

Immobilisation of the Bacteriorhodopsin-polymerase Complex

Immobilisation of the bacteriorhodopsin-polymerase to the sensor chip was carried out according to Jönsson et al Biotechniques (1991); 11:620–627. Briefly, the sensor chip environment was equilibrated with Hepes buffer (10 mM Hepes, 150 mM NaCl, 0.05% surfactant P20 (BIAcore AB, Uppsala, Sweden), pH 7.4). Equal volumes of N-hydroxysuccinimide (0.1 M in water) and N-ethyl-N'-(dimethylaminopropyl)carbodiimide (EDC) (0.1 M in water) were mixed together and injected across the chip (CM5) surface, to activate the carboxymethylated dextran. The bacteriorhodopsin-polymerase was mixed with 10 mM sodium acetate (100 $\mu$l, pH 5) and injected across the activated surface. Finally, residual N-hydroxysuccinimide esters on the sensor chip surface were reacted with ethanolamine (35 $\mu$l, 1 M in water, pH 8.5), and non-bound bacteriorhodopsin-polymerase was washed from the surface. The immobilisation procedure was performed with a continuous flow of Hepes buffer (5 $\mu$l/min) at a temperature of 25° C.

Oligonucleotides

The non-active target and primer oligonucleotides defined as SEQ ID No.1 and SEQ ID No.2 in WO-A-99/05315 were used. The two polynucleotides were reacted under hybridising conditions-to form the target-primer complex.

The primed DNA was then suspended in buffer (20 mM Tris-Hcl, pH 7.5, 8 mM $MgCl_2$, 4% (v/v) glycerol, 5 mM dithiothreitol (DDT), 40 mg bovine serum albumin) containing 60 mM carbonyldiphosphate (to maintain complex integrity) and 80 mM thioredoxin and injected over the chip surface and allowed to bind to the bacteriorhodopsin-polymerase complex via the formation of a bacteriorhodopsin/polymerase/thioredoxin/DNA complex.

DNA Synthesis

This step was carried out using the apparatus shown in FIG. 1 of WO-A-99/05315, but using only one focusing assembly (5) for pulsing monochromatic light into the cell.

The first desired nucleotide to be part of the newly synthesised polynucleotide is introduced into the fluidic cell (6) at a flow rate of 30 $\mu$l/min, at a temperature of 25° C. and a data collection rate of 10 Hz. As the nucleotides pass the focusing assembly (5), monochromatic light is tuned across the wavelength band 300–600 nm (via a solid-sate diode tunable laser) whilst the SPR signal is monitored. Once the SPR signal indicates that conformational nucleotide addition has taken place, the wavelength of the applied laser pulse is maintained. Then Hepes buffer only is allowed to flow over the chip surface for 10 seconds at a flow rate of 30 $\mu$l/min to remove unreacted nucleotides. Subsequently, the next desired nucleotide is added and the cycle repeated for the desired length of polynucleotide.

Alternatively, all nucleotides may be injected into the flow cell at once at a flow rate of 30 $\mu$l/min and the incident monochromatic laser light attenuated across the wavelength range 300–600 nm such that the desired nucleotides are added in the desired sequence.

What is claimed is:

1. A method for polynucleotide synthesis, comprising the steps of:
   (i) reacting a polymerase enzyme with a nucleotide substrate under conditions suitable for polymerase enzyme activity; and
   (ii) modulating the conformation of the polymerase enzyme by applying monochromatic light to allow incorporation of a predetermined nucleotide, wherein the polymerase enzyme is immobilized on a support material, and wherein the polymerase enzyme comprises a biological photonic transducer molecule which modulates the polymerase enzyme active site conformation when contacted with the monochromatic light.

2. The method according to claim 1, wherein the conformation is modulated by surface plasmon resonance.

3. The method according to claim 1, wherein the conformation is modulated by a laser.

4. The method according to claim 1, wherein the polymerase enzyme is fixed within the field of applied monochromatic light.

5. The method according to claim 1, wherein the biological photonic transducer molecule is bacteriorhodopsin.

* * * * *